United States Patent
Filippatos et al.

(10) Patent No.: US 10,881,291 B2
(45) Date of Patent: Jan. 5, 2021

(54) EYE SURGERY SYSTEM

(71) Applicant: CARL ZEISS MEDITEC AG, Jena (DE)

(72) Inventors: Konstantinos Filippatos, Munich (DE); Artur Högele, Oberkochen (DE); Thorsten Tritschler, Aalen (DE); Christoph Hauger, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 470 days.

(21) Appl. No.: 15/800,433

(22) Filed: Nov. 1, 2017

(65) Prior Publication Data

US 2018/0064332 A1 Mar. 8, 2018

Related U.S. Application Data

(63) Continuation of application No. 14/796,023, filed on Jul. 10, 2015, now abandoned.

(30) Foreign Application Priority Data

Jul. 10, 2014 (DE) .................. 10 2014 010 350

(51) Int. Cl.
*A61B 3/10* (2006.01)
*A61B 90/20* (2016.01)
(Continued)

(52) U.S. Cl.
CPC ............ *A61B 3/102* (2013.01); *A61B 3/0025* (2013.01); *A61B 3/0033* (2013.01);
(Continued)

(58) Field of Classification Search
CPC ........... A61B 3/12; A61B 3/13; A61B 3/1216; A61B 3/1241; A61B 3/102; A61B 3/10;
(Continued)

(56) References Cited

U.S. PATENT DOCUMENTS 4,803,352 A * 2/1989 Bierleutgeb ........... G02B 21/18
250/201.3
5,066,969 A * 11/1991 Kawasaki .............. G03B 17/14
396/257
(Continued)

FOREIGN PATENT DOCUMENTS

DE 102005042436 A1 4/2007
DE 102008034490 A1 2/2010
(Continued)

OTHER PUBLICATIONS

The Use of Optical Coherence Tomography in Intraoperative Ophthalmic Imaging, Hahn et al. Ophthalmic Surg Lasers Imaging. Jul. 2011. (Year: 2011).*
(Continued)

*Primary Examiner* — Travis S Fissel
(74) *Attorney, Agent, or Firm* — Patent Portfolio Builders PLLC

(57) ABSTRACT

An eye surgery system 1 comprises microscopy optics 3 and an OCT device 5 to generate a light-optical image and an OCT image of an eye fundus 11, a controller 29 and a visualization system 13, 41, 83. The controller comprises a data interface 97 for receiving a preoperative OCT image and may control the visualization system to display a representation of the received preoperative OCT image. The controller may control the OCT device 5 to record an intraoperative OCT image and may control the visualization system to display a representation of the recorded intraoperative OCT image. The controller may adjust a magnification of the representation of the intraoperative OCT image and/or a magnification of the representation of the preoperative OCT image so that the magnifications of the representation of the intraoperative OCT image and the magni-
(Continued)

fication of the representation of the preoperative OCT image are equal.

25 Claims, 4 Drawing Sheets

(51) Int. Cl.
    *A61B 3/00*     (2006.01)
    *A61B 3/12*     (2006.01)
    *A61B 3/13*     (2006.01)
    *A61F 9/007*     (2006.01)
    *A61B 3/125*     (2006.01)
    *A61B 90/00*     (2016.01)

(52) U.S. Cl.
    CPC .......... *A61B 3/0058* (2013.01); *A61B 3/1225* (2013.01); *A61B 3/13* (2013.01); *A61B 90/20* (2016.02); *A61B 3/125* (2013.01); *A61B 2090/3735* (2016.02); *A61F 9/007* (2013.01)

(58) Field of Classification Search
    CPC ............. A61B 5/14555; A61B 5/0033; A61B 5/0035; A61B 8/13; A61B 2090/3762
    USPC ........ 351/206, 205, 208, 654, 221, 245, 246
    See application file for complete search history.

(56) References Cited

U.S. PATENT DOCUMENTS

| | | | |
|---|---|---|---|
| 2005/0027193 A1* | 2/2005 | Mitschke | A61B 6/12 600/427 |
| 2008/0198329 A1 | 8/2008 | Gaida | |
| 2009/0219483 A1* | 9/2009 | Takanashi | A61B 3/132 351/205 |
| 2009/0257065 A1 | 10/2009 | Hauger et al. | |
| 2011/0122365 A1 | 5/2011 | Kraus et al. | |
| 2012/0071890 A1 | 3/2012 | Taylor et al. | |
| 2012/0092615 A1 | 4/2012 | Izatt et al. | |
| 2012/0105711 A1* | 5/2012 | Kudo | H04N 5/23209 348/360 |
| 2012/0120469 A1 | 5/2012 | Fukushima | |
| 2012/0184846 A1 | 7/2012 | Izatt et al. | |
| 2013/0176336 A1 | 7/2013 | Hannula | |
| 2013/0265545 A1 | 10/2013 | Buckland et al. | |
| 2014/0320626 A1 | 10/2014 | Kim et al. | |

FOREIGN PATENT DOCUMENTS

| | | |
|---|---|---|
| DE | 102011119899 A1 | 6/2013 |
| EP | 2103249 A1 | 9/2009 |
| EP | 2786697 A1 | 10/2014 |
| WO | 2013081252 A1 | 6/2013 |

OTHER PUBLICATIONS

Intraoperative OCT and Vitreoretinal Surgery, Ehlers, Justis, Retina Today Nov. 2011 (Year: 2011).*
Intraoperative Use of Handheld Spectral Domain Optical Coherence Tomography Imaging in Macular Surgery, Retina. 2009 ; 29(10): 1457-1468 (Year: 2009).*
Intraoperative Visualization of Anatomical Targets in Retinal Surgery, Applications of Computer Vision, 2008. (Year: 2008).*
Office Action in related U.S. Appl. No. 14/796,023 dated Mar. 9, 2018.
Fleming, et al.; Intraoperative Visualization of Anatomical Targets in Retinal Surgery; Applications of Computer Vision, IEEE Workshop WACV 2008, Jan. 7-9, 2008; pp. 1-6.
Extended European search report for corresponding EP application No. 15002070.9 dated Sep. 14, 2015.
German Office Action for corresponding DE application No. 10 2014 010 350.1 dated Apr. 17, 2015.
Niemeijer et al., "Registration of 3D spectral OCT volumes combining ICP with a graph-based approach", Proc. of SPIE, vol. 8314, 2012, pp. 1-9.
Wikipedia, "Optische Kohärenztomografie", 2013, http://de.wikipedia.org/w/index.php?title=Optische_Koh%C3%A4renztomografie&oldid=122946781 (https://en.wikipedia.org/wiki/Optical_coherence_tomography).
Office Action in corresponding/related U.S. Appl. No. 14/796,023 dated Oct. 31, 2018.
Pouya, et al.; "Intraoperative Use of Handheld Spectral Domain Optical Coherence Tomography Imaging in Macular Surgery"; Retina 2009, 29:10; Nov.-Dec, 2009; pp. 1457-1468.

* cited by examiner

EYE SURGERY SYSTEM

CROSS-REFERENCES TO RELATED APPLICATIONS

The present application is a continuation of pending U.S. application Ser. No. 14/796,023, filed on Jul. 10, 2015, which claims priority of Patent Application No. 10 2014 010 350.1, filed Jul. 10, 2014 in Germany, the entire contents of which are incorporated by reference herein.

FIELD

The invention relates to eye surgery systems comprising microscopy optics for generating a light-optical image of an eye fundus and an OCT device for generating an OCT image of the eye fundus.

BACKGROUND

Such eye surgery systems may be used to perform surgical interventions at the retina of an eye of a patient. A surgeon may continuously observe the light-optical image of the eye fundus while performing manipulations at the retina of the eye using surgical tools. Further, the surgeon may verify the result of the manipulations using intraoperative OCT images generated during the intervention. For this, it is desirable to compare a current result of the intervention to a preoperative OCT image obtained prior to the intervention to be able to assess a success of the intervention better and to plan further necessary measures. Therefore, it is further desirable to observe and compare the light-optical image generated during the intervention, the OCT image generated during the intervention and the OCT image generated prior to the intervention simultaneously or at least consecutively at short temporal distances.

SUMMARY

It is an objective of the present invention to suggest an eye surgery system of the previously mentioned kind allowing to observe intraoperative OCT images, i.e. OCT images obtained during the intervention, preoperative OCT images, i.e. OCT images obtained before the intervention, and intraoperative light-optical images, i.e. light-optical images obtained before the intervention, of an eye fundus during a surgical intervention. Embodiments of the invention provide an eye surgery system comprising an optical system, a controller and a visualization system. The optical system comprises microscopy optics and an OCT device. The microscopy optics are configured to generate a light-optical image of an eye fundus. The OCT device is configured to scan the eye fundus using an OCT measurement beam and to generate an OCT image of the eye fundus.

The microscopy optics may comprise an objective lens and an auxiliary lens which are disposed close to the eye and which support imaging of the eye fundus. This auxiliary lens may be disposed at a distance from the eye, be mounted separately and generate an image of the eye fundus as an intermediate image which, in turn, is further imaged by the objective lens. Such an auxiliary lens may also be referred to as an ophthalmoscopy magnifying glass. The auxiliary lens may also be in direct contact with the cornea of the eye but does not generate an intermediate image of the eye fundus so that the auxiliary lens and the objective lens together will generate the image of the eye fundus. Such an auxiliary lens may also be referred to as a contact glass. Herein, each of the objective lens and the auxiliary lens may consist of one or plural lens elements and, in particular, may also comprise mirrors. Then, an ocular or a pair of oculars may be disposed in the beam path behind the objective lens, wherein the surgeon may look into the ocular or the pair of oculars using one eye or both his eyes in order to observe the light-optical image of the eye fundus. Furthermore, a camera may be disposed in the beam path behind the objective lens, and detect an image of the eye fundus. Then, the image may be displayed by a visualization system so that the surgeon may observe the image.

The OCT device comprises an interferometer having a reference path and a measurement path where the eye fundus is disposed so that an OCT measurement beam generated by the OCT device is incident onto the eye fundus and an interference of measurement light reflected or backscattered from the eye fundus with measurement light having passed the reference path is detected. Furthermore, the OCT device may comprise deflector elements for the OCT measurement beam to scan the OCT measurement beam across the eye fundus and to generate the OCT image of the eye fundus thereby.

The OCT device and the microscopy optics may share same optical components. For example, the OCT measurement beam may traverse the auxiliary lens, such as an ophthalmology magnifying glass or a contact glass, or the objective lens of the microscopy optics.

According to exemplary embodiments, the microscopy optics comprise at least one ocular for generating a representation the light-optical image of the eye fundus and a display apparatus for displaying a representation of the OCT image generated by the OCT device, wherein the visualization system further comprises optics configured to project the representation of the OCT image displayed by the display apparatus into a beam path of the at least one ocular so that the representation of the OCT image and the representation of the light-optical image may be observed in the at least one ocular. Herein, the visualization system may be configured so that the representation of the light-optical image and the representation of the OCT image are displayed simultaneously and be adjacent, e.g. next to each other. That is, an observer may observe the representation of the light-optical image and the representation of the OCT image while the representations are located adjacent to each other. Furthermore, the light optical image and the OCT image may be displayed in superposition, i.e. representations of both images may fully or partially overlap each other.

According to further embodiments, the microscopy optics comprise a camera configured to detect the light-optical image of the eye fundus and the visualization system comprises a display to display a representation of the detected light-optical image and a representation of the generated OCT image. Also herein, the representation of both images may be displayed by the display simultaneously and be adjacent to each other, e.g. next to each other or spatially overlapping each other. Furthermore, both images may be displayed simultaneously and be overlapping or be displayed consecutively so that either the representation of the light-optical image or the representation of the OCT image may be observed at a single point in time.

According to further exemplary embodiments, the controller controls, e.g. invokes, the visualization system to display the representation of the OCT image. When the light-optical image is detected by a camera, the controller controls the visualization system to display the representation of the image.

According to exemplary embodiments, the controller comprises a data interface to receive a preoperative OCT image. Then, the controller may control the visualization system to display a representation of the received preoperative OCT image as well as the representation of the intraoperative OCT image. Also herein, representations of the received preoperative OCT image and the intraoperative OCT image may be displayed simultaneously or consecutively and be adjacent, e.g. next to each other or overlapping each other.

According to exemplary embodiments herein, the controller is configured to adjust a magnification of the representation of the intraoperative OCT image and/or a magnification of the representation of the preoperative OCT image. According to exemplary embodiments herein, the controller is further configured to display representations of the intraoperative OCT image and the preoperative OCT image at same magnifications by the visualization system. This is especially favorable for the surgeon as he may compare both representations of the OCT images to each other particularly well and may plan further steps based on this comparison.

According to exemplary embodiments, the controller is further configured to adjust the magnifications of the representations so that, besides the intraoperative OCT image and the preoperative OCT image, also the representation of the intraoperative light-optical image is displayed at the same magnification.

Two representations of images of the eye fundus may be regarded as to have the same magnification if a distance between two structures of the eye fundus visible in both representations have the same distance in the representations of both images.

According to exemplary embodiments herein, the controller is further configured to adjust an orientation of the representation of the intraoperative OCT image and/or an orientation of the representation of the preoperative OCT image. According to further exemplary embodiments herein, the controller is further configured to control the visualization system to display the representation of the intraoperative OCT image and the representation of the preoperative OCT image at same orientations. In this case, the surgeon may compare these two representations of images to each other particularly well and plan further steps based on this comparison.

According to further embodiments, the controller is further configured to adjust the orientations of the representations so that, besides the intraoperative OCT image and the preoperative OCT image, also the representation of the intraoperative light-optical image is displayed at a same orientation by the visualization system.

Two representations of images of the eye fundus may be regarded as to have a same orientation if a straight line in the representation of a first one of the two images and a straight line in the representation of a second one of the two images have a same orientation, wherein each of the straight lines connects two structures of the eye fundus, which structures are visible in both representations. That is, the straight line connecting the two structures in the representation of the first image is orientated parallel to the straight line connecting the respective structures in the representation of the second image.

According to exemplary embodiments, the controller is configured to perform an image analysis of the preoperative OCT image and an image analysis of the intraoperative OCT image and to adjust, based on these image analyses, the magnification and/or the orientation of the representation of the intraoperative OCT image and/or the magnification and/or the orientation of the representation of the preoperative OCT image so that both representations of the OCT images are displayed at the same magnification and orientation, respectively.

According to exemplary embodiments, if both OCT images are displayed simultaneously in superposition or consecutively in a common region of the display, i.e. the representations of the images overlap each other, the controller may displace one of or both representations of the images by translation so that each structure of the eye fundus in both representations is displayed at a same location on the display.

The image analysis may recognize patterns in both OCT images and identify differences between both images by comparing the patterns. The controller may change the orientation of the representation of the images or displace them relative to each other on the display based on these differences.

According to further exemplary embodiments, the controller may obtain differences of the magnifications of the representation of the preoperative OCT image and the representation of the intraoperative OCT image by detecting at least one optical parameter of the recorder apparatus. Based on the detected at least one optical parameter, the controller may adjust the magnification of the representation of the preoperative OCT image and/or the magnification of the representation of the intraoperative OCT image so that the magnifications are equal. Herein, the magnification of the preoperative OCT image may be predetermined and, for example, determined by a diagnostics system configured to record the preoperative OCT image. Herein, the preoperative OCT image received via the data interface may always have the same predetermined magnification or different magnifications, the respective values of which may then be transmitted to the controller by the data interface together with the preoperative OCT images so that the value of the magnification of the received preoperative OCT image may be available to the controller. The controller may compare the value with the magnification of the intraoperative OCT image, wherein the magnification of the intraoperative OCT image may be deduced from the detected at least one optical parameter of the recorder apparatus.

The at least one optical parameter of the recorder apparatus may represent a focal length of an objective lens of the optical system and/or a focal length of an auxiliary lens of the optical system such as an ophthalmoscopy magnifying glass or a contact glass. The at least one optical parameter may further represent a magnification of a zoom system disposed in the beam path of the microscopy optics.

The focal lengths of the objective lens or the zoom system may be predetermined, always be the same or be changeable. If the focal lengths are changeable, the recorder apparatus may comprise sensors configured to detect the focal lengths based on, for example, distances between individual lens elements of the objective lens and the zoom system, respectively. Furthermore, the focal lengths of the objective lens or the zoom system may be adjusted by actuators controlled by the controller so that respective focal lengths and parameters representing these focal lengths are available to the controller.

According to exemplary embodiments, plural auxiliary lenses, such as ophthalmoscopy magnifying glasses or contact glasses, having different focal lengths may be provided and individually selected to be disposed in the beam path of the optical system. In order to obtain the focal lengths of the auxiliary lens currently in use, the controller may comprise a user interface configured to receive data from a user, the data providing for identification of the auxiliary lens disposed in the beam path of the optical system. Alternatively or in addition, the controller may be configured to determine the auxiliary lens disposed in the beam path of the optical system. This determination may be performed according to various kinds. For example, the controller may control the OCT device to perform measurements of distances between surfaces of lens elements of the auxiliary lens and identify the auxiliary lens in use based on the measured distances. Furthermore, the different auxiliary lenses may have different marks on its lens carriers, the marks being visible in the light-optical image generated by the microscopy optics. By detecting and analyzing this image, the controller may identify the auxiliary lens in use based on the detected marks. Furthermore, the different auxiliary lenses may have different electrical or mechanical identifiers readable by suitable electrical or mechanical contacts, the contacts in turn being readable at a mount of the auxiliary lens in the beam path.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

Hereinafter, embodiments of the invention are illustrates with reference to Figures of which.

DETAILED DESCRIPTION OF EXEMPLARY EMBODIMENTS

Figure 1:
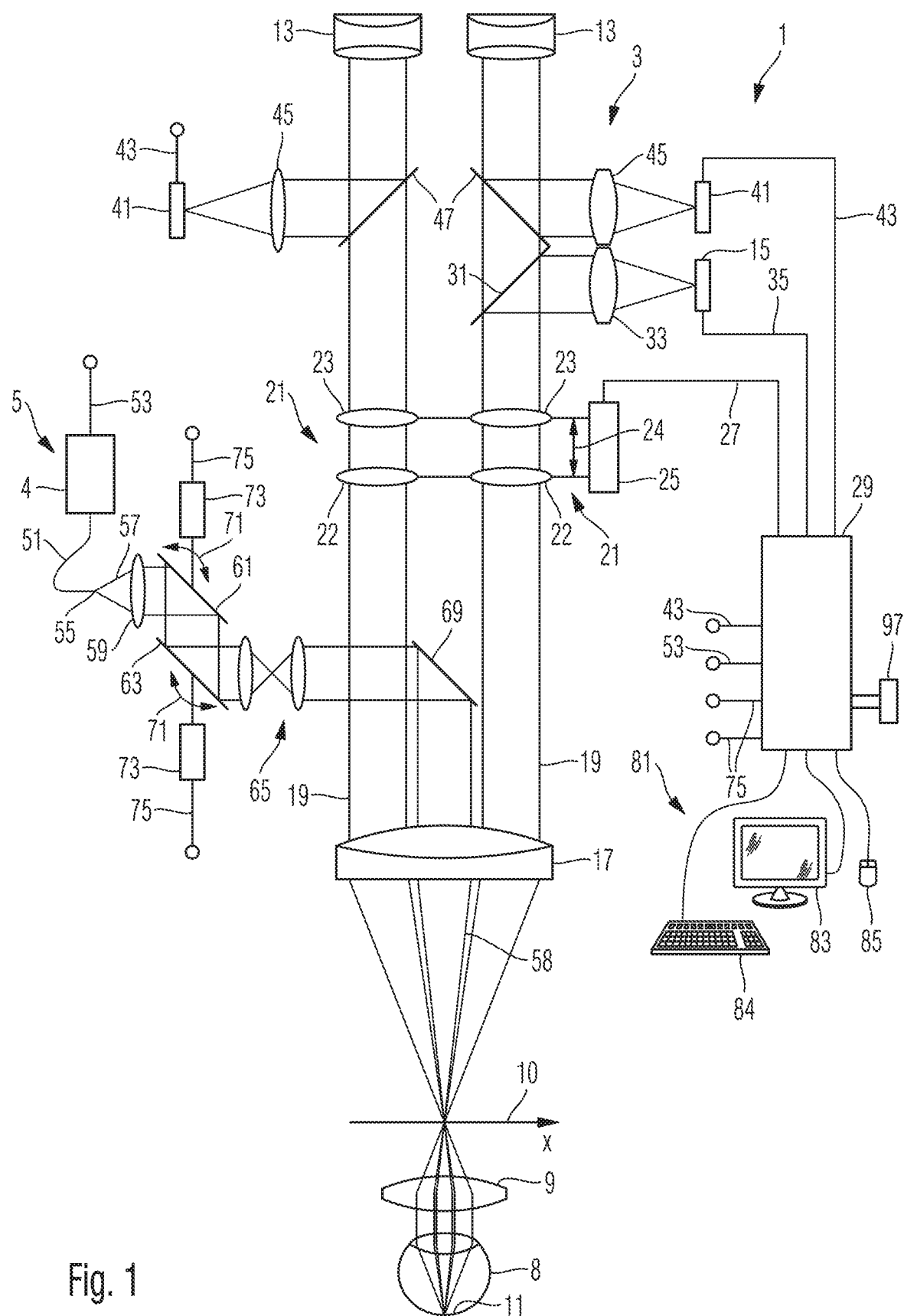
FIG. 1 shows a schematic illustration of an eye surgery system.

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

FIG. 1 is a schematic illustration of an eye surgery system 1. The eye surgery system 1 comprises microscopy optics 3 configured to generate light-optical images of an eye fundus 11 of an eye 8. The fundus 11 is imaged by the microscopy optics 3 of the illustrated exemplary embodiment by a pair of oculars 13 on the one hand, into which a surgeon may look with both his eyes, and on the other hand by a camera 15 which may record images of the fundus 11 and generate data representing the images.

For this, the microscopy optics 3 comprise an auxiliary lens 9 implemented as an ophthalmoscopy magnifying glass and generating an intermediate image of the fundus 11 in a plane 10. The microscopy optics 3 further comprise an objective lens 17 which may consist of one or plural lens elements and, in particular, may image the intermediate image formed in the plane 10 to infinity as shown in the illustrated example. In the beam path behind the objective lens 17, each of two partial beam bundles 19 passes a zoom lens assembly 21 capable of changing an imaging scale of the optics. For this, each of both zoom lens assemblies 21 may comprise at least two lens groups 22 and 23 which are displaceable relative to each other in direction of the partial beam bundle 19 as indicated by an arrow 24 in FIG. 1. The displacement of the lens groups 22 and 23 relative to each other is controlled by an actuator 25 which, in turn, is controlled by a controller 29 via a control wire 27 in order to adjust the imaging scale of the microscopy optics 3.

Behind the zoom lens assemblies 21, each of the partial beam bundles 19 enters one of the oculars 13. From the partial beam bundle 19 located on the right side in FIG. 1, a portion of the light of the partial beam bundle 19 is deflected by a partially transparent mirror 31 and directed onto the camera 15 by camera adapter optics 33 so that the camera 15 may detect the image of the field of view of the object region where the eye fundus 11 is located. The data generated by the camera 15 are transmitted to the controller 29 via a data wire 35.

The microscopy optics 3 further comprise two electronic image displays 41 fed with image data from the controller 29 via the data wire 43. Representations of the images displayed by the image displays 41 are each projected into the beam path towards the oculars 13 by projection optics 45 and a partially transparent mirror 47 disposed in the partial beam bundle 19 so that the surgeon looking into the oculars 13 may perceive the representations of the images displayed by the image displays 41 in superposition with the light-optical image of the field of view of the object region 11.

The eye surgery system 1 further comprises an OCT device 5 for performing OCT measurements. The OCT device 5 comprises an OCT assembly 4 having a suitable light source of short coherence and an interferometer, both not illustrated in FIG. 1. OCT measurement light is emitted from the OCT assembly 4 via a light guide fiber 51 so that the OCT measurement light may be incident onto an object to be measured, such as the eye fundus, and measurement light returning from the object may reenter the fiber so that the OCT assembly 4 may examine this returned measurement light and output data representing the measurement. In particular, the OCT assembly 4 may perform a depth scan also referred to as A-scan, the data of which represent intensities of backscattered measurement light in dependence of the depth. The OCT assembly 4 is controlled by the controller 29 via a control and date wire 53. The controller 29 also receives the measurement data generated by the OCT device 5 via this wire 53. The OCT device 5 further comprises collimator optics 59 which collimate OCT measurement light 57 emitted from an end 55 of the fiber 51 to a measurement light beam 58. The measurement light beam 58 is deflected at two deflection mirrors 61 and 63, passes projection optics 65, is incident onto a mirror 69 and is directed onto the fundus 11 by the mirror 69 through the objective lens 17 and the auxiliary lens 9. A portion of the OCT measurement light is backscattered at the fundus 11 so that the backscattered measurement light passes the reverse path through the auxiliary lens 9 and the objective lens 17, the projection optics 65 and the collimator optics 59 so that at least a portion of this light is coupled into the fiber 51 and returns to the OCT assembly 4 where it is examined using the interferometer.

The mirrors 61 and 63 are pivotable in order to deflect the OCT measurement beam so that, by adjusting the pivot positions of the mirrors 61 and 63, the OCT measurement beam 58 may be incident onto selectable locations of the fundus 11. Pivotability of the mirrors 61 and 63 is indicated by arrows 71 in FIG. 1. The pivot positions of the mirrors 61 and 63 are adjusted by actuators 73 controlled by the controller 29 via control wires 75. By controlling the actuators 73, the controller 29 may scan the fundus 11 using the OCT measurement beam and may generate an intraoperative OCT image of the fundus 11.

The controller 29 further comprises a user interface comprising a screen 83 of a visualization system and a keyboard 84 and a mouse 85 as input media. The visualization system also comprises the displays 41 for feeding representations of images generated by the controller 29 into the beam paths towards the oculars.

In the exemplary embodiment described herein, the eye surgery system is used to perform a microsurgical intervention at the fundus 11 using a surgical tool.

Figure 3:
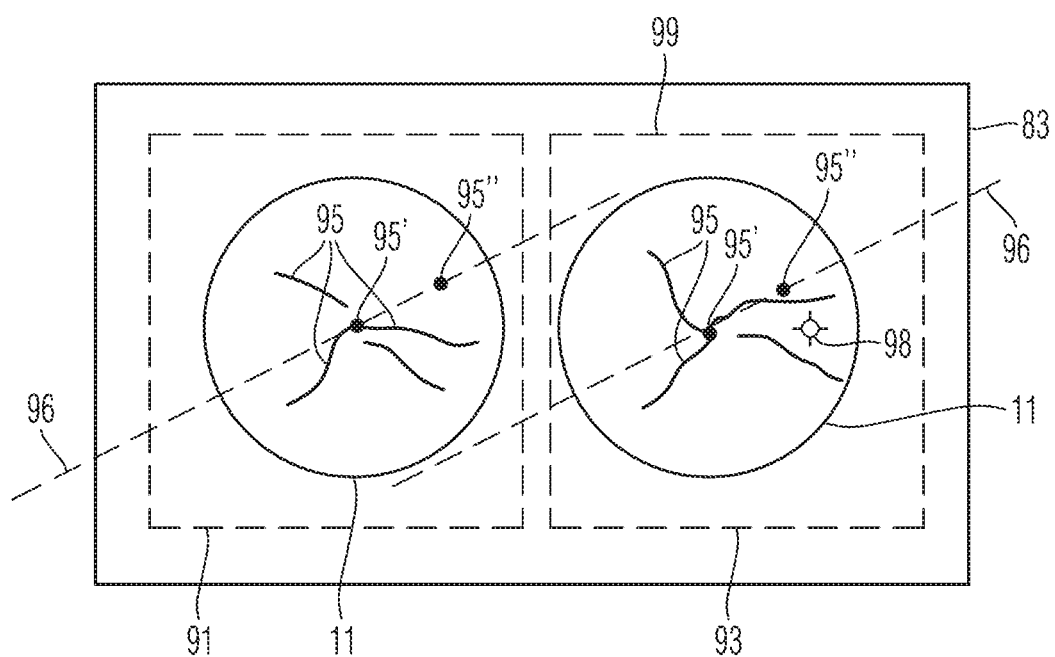
FIG. 3 shows a schematic illustration of a display of a visualization system of the eye surgery system of FIG. 1.

For this, the surgeon observes the representation of the light-optical image of the fundus and the representation of the intraoperative OCT image through the ocular, the representation of the OCT image being projected via the display 41 and the optics 45. Alternatively, the surgeon may observe representations of the light-optical image and the intraoperative OCT image on the screen 83. An example of such representations is schematically illustrated in FIG. 3. FIG. 3 shows the screen 83 and images of the fundus displayed thereon. A representation of an image 91 shown on the left side in FIG. 3 is the representation of the light-optically image of the fundus 11 detected by the camera 15, whereas a representation of an image 93 shown on the right side of FIG. 3 is the representation of the intraoperative OCT image of the fundus 11 generated by the OCT device 5. Structures of the fundus 11 are schematically sketched by lines 95 in FIG. 3. Due to the different recording techniques used to obtain the images 91 and 93, the structures 95 contained in the images are not identical, however they are similar. Based on a comparison of the representations of the images, the surgeon may obtain valuable information.

Figure 2:
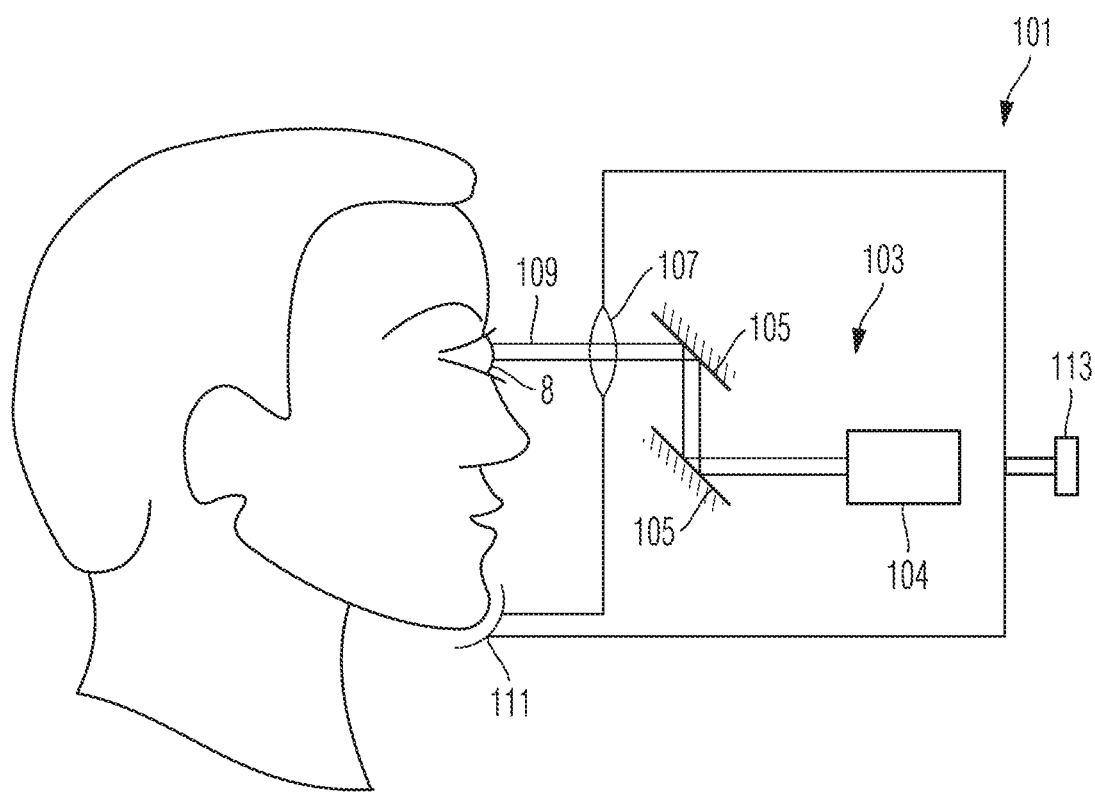
FIG. 2 shows a schematic illustration of a diagnostics system which may be part of the eye surgery system of FIG. 1.

The eye surgery system 1 is further configured to display a representation of the preoperative OCT image of the fundus by the visualization system. FIG. 2 is a schematic illustration of a diagnostics system 101 for generating the preoperative OCT image. The diagnostics system 101 comprises an OCT device 103 having an OCT assembly 104, which comprises a light source of short coherence and an interferometer, scan mirrors 105 and optics 107 to generate a measurement light beam 109. The patient rests, for example, his chin onto a rest element 111 so that the measurement light beam 109 may enter the eye 8. The scan mirrors 105 are controlled so that a focus of the measurement light beam 109 scans the fundus of the eye 8 of the patient to generate a preoperative OCT image of the fundus. The OCT image is output via a data interface 113.

The controller 29 comprises a data interface 97 to receive the preoperative OCT image and may display a representation of it by the visualization system. The representation of the preoperative OCT image may be displayed, for example as an image 99 (see FIG. 3) instead of the intraoperative OCT image 93, next to the representation of the light-optical image 91 of the fundus 11. In particular, the representations of the preoperative OCT image 99 and the intraoperative OCT image 93 may be displayed consecutively and alternately. Also, using the input medium such as the keyboard 84 and the mouse 85, the user may select which of the OCT images is/are to be displayed. Further, representations of the three images, i.e. the light-optical image 91, the intraoperative OCT image 93 and the preoperative OCT image 99, may be displayed next to each other.

For each of the previously described ways of displaying the representations of the images 91, 93 and 99, it is desirable that these representations are displayed at a same magnification, a same orientation and are disposed relative to each other so that corresponding structures 95 of the fundus 11 are located at corresponding locations in the representations of the images 91, 93 and 99. For this, the controller 29 is configured to adjust the magnification of the representation of the intraoperative OCT image 93 and/or the magnification of the representation of the preoperative OCT image 99 via the visualization system. Furthermore, the controller may change an orientation of the representation of the intraoperative OCT image 93 relative to the orientation of the representation of the preoperative OCT image 99. Also, the controller may displace the image contents of the intraoperative OCT image 93 and the preoperative OCT image 99 by translation. To determine the correct values of the magnifications, the orientations and the translations of the representations of the images, the controller 29 may perform an image analysis of the images and identify structures 95 visible therein. By comparing the structures or suitable portions of the structures, the controller may determine values for adjusting the magnifications, orientations and translations. Suitable structures may be, for example, structures of the macula, structures of the visual nerve or blood vessels.

The controller may further analyze the light-optical image 91 by image analysis and identify the structures 95 visible in the light-optical image. By another comparison between suitable structures contained in the light-optical image 91 and one of or both of the OCT images 93 and 99, the controller may adjust the magnification, the orientation and the translation of the representations of the OCT images 93 and 99 so that corresponding structures are displayed at the same locations in the representations of the three images. This is illustrated in FIG. 3: structures 95' and 95" on the fundus are shown in all three images as spots. The distances between representations of both structures 95', 95" are equal in all three images on the screen 83 of the visualization system. Furthermore, a straight line 96 connecting both structures 95' and 95" with each other has the same orientation in the representations of the three images 91, 93, 99 so that, for example, the straight line 96 in the representation of the light-optical image 91 on the screen 83 of the visualization system is parallel to the straight line 96 in the representation of the intraoperative image 93 and parallel to the corresponding straight line in the representation of the preoperative image 99. Furthermore, the representation of the intraoperative image 93 is displaced relative to the representation of the preoperative image 99 so that the locations 95' and 95" in the representation of the intraoperative image 93 coincide with the locations 95' and 95" in the representation of the preoperative OCT image 99 on the screen 83 of the visualization system, respectively.

FIG. 3 shows a mark 98 displayed by the controller 29 in the representation of the intraoperative OCT image 93. The representation of this mark is based on a diagnostics mark defined, for example, by a doctor in the preoperative image. For example, the doctor who assists in generating the preoperative OCT image and examines this image, defines the diagnostics mark in the representation of the preoperative OCT image in order to mark a specific location at the fundus for subsequent treatment. Therefore, the diagnostics mark may support planning of the surgical intervention. For example, this may be done in that the doctor observes the representation of the preoperative OCT image on a screen of a computer system and generates the mark using an input medium of the computer system. A suitable software of the computer system may store the image coordinates of this diagnostics mark as data pertaining the preoperative OCT image.

The controller 29 may obtain these image coordinates of the diagnostics mark together with the preoperative OCT image via the data interface 97. Then, having adjusted the magnification, the orientation and the translation of the representation of the preoperative OCT image on the screen 83 of the visualization system, the controller 29 may also display the mark 98 on the screen at a location in the representation of the intraoperative OCT image, the location corresponding to the location of the diagnostics mark in the preoperative OCT image.

Instead or in addition to the determining of the required magnifications, rotations and translations of the images based on an image analysis, it is also possible to determine the magnifications of the images by determining parameters of the optics in use. For example, the magnification of the diagnostics system 101 used during recording of the preoperative OCT image may be fixed, unchangeable and predetermined. The magnifications of the light-optical images visible via the oculars 13 or the screen 83 may be determined from parameters of the microscopy optics 3. These parameters may comprise adjustment values used to adjust the zoom system 21 which is, in turn, controlled by the controller 29 via the actuator 25; hence the adjustment values are available to the controller. In addition, the focal lengths of the objective lens 17 and the auxiliary lens 9 are parameters influencing the magnification of the light-optical image. If the objective lens 17 has a fixed focal length, the focal length is available to the controller 29. If this focal length is changeable, for example by two lens elements of the objective lens 17 being displaceable relative to each other, the distances of the two lens elements from each other may be obtained by a sensor of the controller 29. The controller may also control these distances by an actuator similar to the actuator used to control the zoom system 21 so that values of the selected adjustment are available to the controller 29.

The focal length of the auxiliary lens 9 may be predetermined. Often, it is desirable to use auxiliary lenses of different focal lengths. In this case, it is necessary that the type of the auxiliary lens 9 disposed in the beam path is available to the controller 29. This can be achieved by providing a user interface to the controller so that the user may enter data, for example via the keyboard 84 or the mouse 85, identifying the auxiliary lens 9 currently in use. Furthermore, the controller may control the OCT device 5 to measure distances between surfaces of lens elements of the auxiliary lens 9. Based on the measured distances, the controller 29 may determine the type of the auxiliary lens in use. Furthermore, the different auxiliary lenses may have different identifiers detectable by the eye surgery system 1. Three examples of such identifiers are described hereinafter with reference to FIG. 4.

Figure 4:
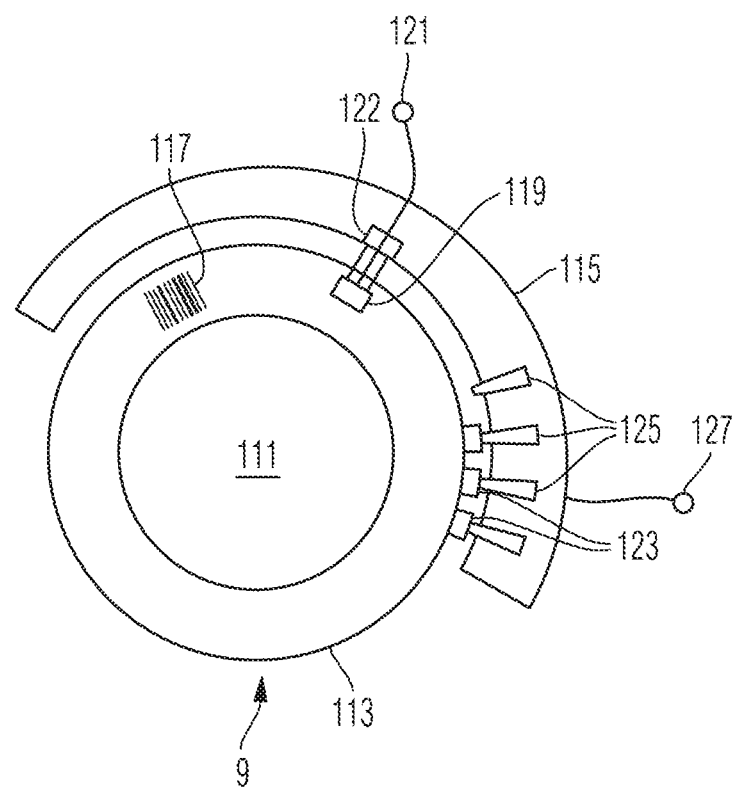
FIG. 4 shows a schematic top view onto an ophthalmoscopy magnifying glass and its mount.

FIG. 4 schematically shows a top view onto an auxiliary lens, namely an ophthalmology magnifying glass 9 disposed in the beam path of the eye surgery system. The ophthalmology magnifying glass 9 comprises a lens element 111 and a carrier 113 of the lens element 111. The carrier 113 is mounted to a mount 115 holding the ophthalmology magnifying glass 9 in the beam path of the eye surgery system 1. A first option of an identifier identifying the ophthalmology magnifying glass 9 is an optical mark 117 such as a bar code. The optical mark 117 is arranged on the carrier 113 so that it is visible in the top view of FIG. 4. Accordingly, the optical mark 117 is also visible in the light-optical image recorded by the camera 15 and, hence, may be identified by the controller 29 through image analysis. For improving the result of such an image analysis, it may be helpful to change the setting of the microscopy optics so that the mark 117 is as sharply visible as possible in the light-optical image.

A second option of an identifier is provided by an electrical storage element 119 fixed to the carrier 113 and comprising data identifying the ophthalmology magnifying glass 9. The content of the storage element 119 may be read by the controller via a date wire 121 connected to the memory element 119 via a plug contact 122 when the ophthalmology glass 9 is disposed at the mount 115.

A third option for an identifier is a mechanical identifier. As illustrated, the mechanical identifier may be implemented by three projections 123 provided on the carrier 113, the three projections 123 operating three out of four switches 125 provided at the mount 115. A fourth switch of the four switches 125 is not operated in the illustrated example as a projection 123 configured to operate the fourth switch is not provided at the carrier 113. The configuration of the switches 125 may be transmitted to the controller 29 via a date wire 127.

Therefore, the controller 29 is capable of determining the magnification of the recorded light-optical image based on parameters of the microscopy optics 3. This is also possible for the magnification of the recorded intraoperative OCT image. In the illustrated example, the beam path of the OCT measurement light passes through the objective lens 17 and the ophthalmology magnifying glass 9. Their focal lengths and parameters representing the focal lengths as described above may be determined. In addition, the magnification of the recorded OCT image is determined by parameters defined, for example, by the pivot positions of the mirrors 61 and 63 for scanning the fundus. Also, these parameters may be available to or controlled by the controller 29. Therefore, also the magnification of the recorded intraoperative OCT image may be determined and compared to the magnification of the preoperative OCT image to adjust the magnifications selected for the representation by the visualization system so that the displayed OCT images have the same magnifications.

Figure 5:
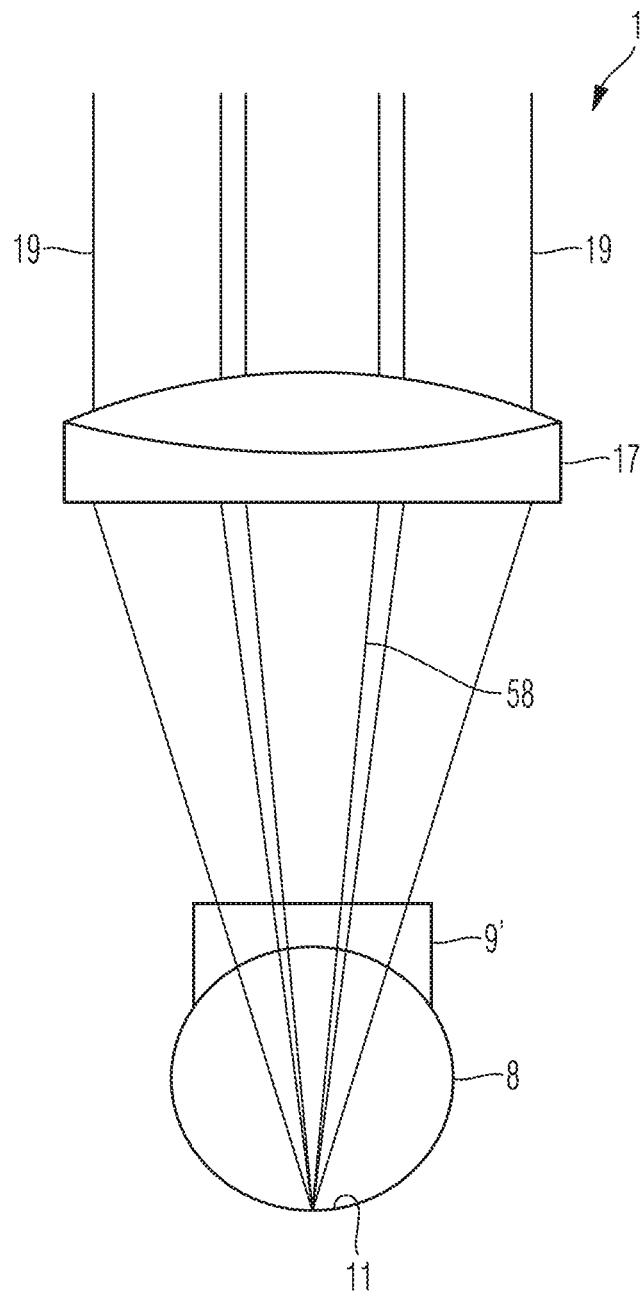
FIG. 5 shows a schematic illustration of a portion of another eye surgery system.

FIG. 5 is a schematic illustration of a portion of an eye surgery system 1 having a setup which is very similar to the setup of the eye surgery system shown in FIG. 1. In contrast to the eye surgery system shown in FIG. 1, the eye surgery system 1 of FIG. 5 does not use an ophthalmology magnifying glass but a contact glass 9' for imaging the fundus 11. While the ophthalmology magnifying glass generates an intermediate image of the fundus to be further imaged by the objective lens, the contact glass 9' does not generate an intermediate image of the fundus 11 so that the (first) image of the fundus 11 is formed in the beam path behind the objective lens 17.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

The invention claimed is:

1. An eye surgery system for assisting an eye surgery, the eye surgery system comprising:
   an optical system including microscopy optics and an OCT device, wherein the microscopy optics comprise an objective lens and are configured to generate a light-optical image of an eye fundus, and wherein the OCT device is configured to scan the eye fundus using an OCT measurement beam passing through the objective lens and to generate an OCT image of the eye fundus;
   a controller; and
   a visualization system;
   wherein the controller comprises a data interface to receive a preoperative OCT image and is configured to control the visualization system to display a representation of the preoperative OCT image,
   wherein the controller is further configured to control the OCT device to record an intraoperative OCT image and to control the visualization system to display a representation of the recorded intraoperative OCT image,
   wherein the controller is further configured to adjust at least one property of a group of properties so that all conditions of a first group of conditions is fulfilled,
   the group of properties comprising a magnification of the representation of the intraoperative OCT image, a magnification of the representation of the preoperative OCT image, an orientation of the representation of the intraoperative OCT image and an orientation of the representation of the preoperative OCT image,
   the first group of conditions comprising:
      the magnification of the displayed representation of the intraoperative OCT image and the magnification of the displayed representation of the preoperative OCT image be equal; and
      the orientation of the displayed representation of the intraoperative OCT image and the orientation of the displayed representation of the preoperative OCT image be equal,
   wherein the microscopy optics further comprise a camera to detect the light-optical image of the eye fundus, and wherein the controller is further configured to control the camera to record the light-optical image and to control the visualization system to display a representation of the recorded light-optical image,
   wherein the controller is further configured to adjust the at least one property of the group of properties so that all conditions of a second group of conditions is fulfilled,
   the second group of conditions comprising:
      the magnification of the displayed representation of the intraoperative OCT image and the magnification of the displayed representation of the preoperative OCT image be equal to a magnification of the representation of the light-optical image displayed by the visualization system; and
      the orientation of the displayed representation of the intraoperative OCT image and the orientation of the displayed representation of the preoperative OCT image be equal to an orientation of the representation of the light-optical image displayed by the visualization system.

2. The eye surgery system according to claim 1, wherein the controller is further configured to control the visualization system so that the representation of the preoperative OCT image and the representation of the intraoperative OCT image are displayed simultaneously and are adjacent to each other.

3. The eye surgery system according to claim 2, wherein the representation of the preoperative OCT image and the representation of the intraoperative OCT image are not overlapping each other.

4. The eye surgery system according to claim 2, wherein the representation of the preoperative OCT image and the representation of the intraoperative OCT image are overlapping each other.

5. The eye surgery system according to claim 1, wherein the controller is further configured to control the visualization system so that the representation of the preoperative OCT image and the representation of the intraoperative OCT image are displayed consecutively and alternately.

6. The eye surgery system according to claim 5, wherein the representation of the preoperative OCT image and the representation of the intraoperative OCT image are overlapping each other.

7. The eye surgery system according to claim 1, wherein
   the visualization system comprises an ocular of the microscopy optics, a display and optics,
   the ocular is configured to generate a representation of the light-optical image of the eye fundus, and
   the optics are configured to project at least one of the representation of the preoperative OCT image displayed by the display and the representation of the intraoperative OCT image displayed by the display into a beam path of the ocular.

8. The eye surgery system according to claim 1, wherein the controller is further configured to control the visualization system so that the representation of the light-optical image and the representation of one of the preoperative OCT image and the intraoperative OCT image are displayed simultaneously and are adjacent to each other.

9. The eye surgery system according to claim 8, wherein the representation of the light-optical image and the representation of one of the preoperative OCT image and the intraoperative OCT image are not overlapping each other.

10. The eye surgery system according to claim 8, wherein the representation of the light-optical image and the representation of one of the preoperative OCT image and the intraoperative OCT image are overlapping each other.

11. The eye surgery system according to claim 1, wherein the controller is further configured to control the visualization system so that the representation of the light-optical image and the representation of one of the preoperative OCT image and the intraoperative OCT image are displayed consecutively.

12. The eye surgery system according to claim 11, wherein the representation of the light-optical image and the representation of one of the preoperative OCT image and the intraoperative OCT image are overlapping each other.

13. The eye surgery system according to claim 1, wherein the controller is further configured to perform an image analysis of the preoperative OCT image and an image analysis of the intraoperative OCT image, and wherein the adjusting of the at least one property is based on at least one of these image analyses.

14. The eye surgery system according to claim 1, wherein the controller is further configured to detect at least one optical parameter of the optical system, and wherein the adjusting of the at least one property is based on the at least one optical parameter.

15. The eye surgery system according to claim 14, wherein the at least one optical parameter represents at least one focal length of a group of focal lengths, the group of focal lengths comprising a focal length of an objective lens of the optical system and/or a focal length of an auxiliary lens of the optical system.

16. The eye surgery system according to claim 15, wherein the auxiliary lens is one of an ophthalmoscopy magnifying lens and a contact glass.

17. The eye surgery system according to claim 15, wherein plural auxiliary lenses having different focal lengths are provided, wherein each of the plural auxiliary lenses may be selected to be disposed in a beam path of the optical system.

18. The eye surgery system according to claim 17, further comprising a user interface configured to receive data from a user, the data being suitable to identify the auxiliary lens disposed in the beam path of the optical system.

19. The eye surgery system according to claim 17, wherein the controller is configured to identify the auxiliary lens currently disposed in the beam path of the optical system.

20. The eye surgery system according to claim 19, wherein the controller is configured to identify the auxiliary lens disposed in the beam path of the optical system by a measurement using the OCT device.

21. The eye surgery system according to claim 19, wherein the controller is configured to identify the auxiliary lens disposed in the beam path of the optical system by analyzing the light-optical image.

22. The eye surgery system according to claim 19, wherein the plural auxiliary lenses have different identifiers of a group of identifiers comprising electric and mechanical identifiers, and wherein a mount for the auxiliary lens disposed in the beam path is configured so that the controller can identify the identifier of the auxiliary lens disposed in the beam path.

23. The eye surgery system according to claim 1, further comprising a diagnostics system configured to record the preoperative OCT image and to transmit the recorded preoperative OCT image to the data interface of the controller.

24. The eye surgery system according to claim 23, wherein
the diagnostics system is configured to generate mark data representing a selectable location in the preoperative OCT image, and
the controller is configured to receive the mark data via the data interface and to control the visualization system to display a mark at a location in the representation of the intraoperative OCT image, the location corresponding to the selected location in the preoperative OCT image.

25. An eye surgery assistance method for assisting an eye surgery, the eye surgery assistance method comprising:
providing an eye surgery system, which comprises
an optical system including microscopy optics and an OCT device,
wherein the microscopy optics comprise an objective lens and are configured to generate a light-optical image of an eye fundus, and wherein the OCT device is configured to scan the eye fundus using an OCT measurement beam passing through the objective lens and to generate an OCT image of the eye fundus;
a controller; and
a visualization system;
wherein the controller comprises a data interface to receive a preoperative OCT image and is configured to control the visualization system to display a representation of the preoperative OCT image,
wherein the controller is further configured to control the OCT device to record an intraoperative OCT image and to control the visualization system to display a representation of the recorded intraoperative OCT image,
wherein the controller is further configured to adjust at least one property of a group of properties so that all conditions of a first group of conditions is fulfilled,
the group of properties comprising a magnification of the representation of the intraoperative OCT image, a magnification of the representation of the preoperative OCT image, an orientation of the representation of the intraoperative OCT image and an orientation of the representation of the preoperative OCT image,
the first group of conditions comprising:
the magnification of the displayed representation of the intraoperative OCT image and the magnification of the displayed representation of the preoperative OCT image be equal; and
the orientation of the displayed representation of the intraoperative OCT image and the orientation of the displayed representation of the preoperative OCT image be equal,
wherein the microscopy optics further comprise a camera to detect the light-optical image of the eye fundus, and wherein the controller is further configured to control the camera to record the light-optical image and to control the visualization system to display a representation of the recorded light-optical image,
wherein the controller is further configured to adjust the at least one property of the group of properties so that all conditions of a second group of conditions is fulfilled,
the second group of conditions comprising:
the magnification of the displayed representation of the intraoperative OCT image and the magnification of the displayed representation of the preoperative OCT image be equal to a magnification of the representation of the light-optical image displayed by the visualization system; and
the orientation of the displayed representation of the intraoperative OCT image and the orientation of the displayed representation of the preoperative OCT image be equal to an orientation of the representation of the light-optical image displayed by the visualization system;
receiving, using the data interface, a preoperative OCT image of an eye fundus,
wherein, during the eye surgery, the method further comprises
controlling, using the controller, the OCT device of the eye surgery system to record an intraoperative OCT image of the eye fundus;
detecting, using the camera, a light-optical image of the eye fundus;
adjusting, using the controller, at least one property of the group of properties so that all conditions of the first group of conditions and the second group of properties are fulfilled; and
controlling, using the controller, the visualization system to display a representation of the preoperative OCT image, a representation of the intraoperative OCT image and a representation of the light-optical image, all adjusted to have the same magnification and orientation with respect to each other.

* * * * *